United States Patent
Mahler et al.

(10) Patent No.: US 6,450,970 B1
(45) Date of Patent: Sep. 17, 2002

(54) METHOD AND DEVICE FOR DIAGNOSING AN INFLAMMATORY PROCESS

(76) Inventors: Ron Mahler, 14 Yair Stern Street, Herzlia 46412 (IL); Larry Sheiman, 10/2 Pinchas Rosen Street, Herzelia 'B' 46412 (IL)

( * ) Notice: Subject to any disclaimer, the term of this patent is extended or adjusted under 35 U.S.C. 154(b) by 0 days.

(21) Appl. No.: 09/440,901

(22) Filed: Nov. 16, 1999

(51) Int. Cl.[7] .............................................. A61B 5/00
(52) U.S. Cl. ...................................................... 600/549
(58) Field of Search ................................ 600/549, 559

(56) References Cited

U.S. PATENT DOCUMENTS

| | | | |
|---|---|---|---|
| 5,167,235 A | * 12/1992 | Seacord et al. | 600/549 |
| 5,653,239 A | 8/1997 | Pompei et al. | 128/664 |
| 5,790,586 A | 8/1998 | Hilton, Jr. et al. | 374/131 |
| 5,833,367 A | * 11/1998 | Cheslock et al. | 374/158 |

FOREIGN PATENT DOCUMENTS

| | | |
|---|---|---|
| FR | 71.26367 | 3/1972 |
| GB | 2 319 336 A | 5/1998 |
| WO | WO 92/10133 | 6/1992 |

OTHER PUBLICATIONS

"Concurrent Concepts": Otitis Media in Chidren, New England Journal of Medicine, Jun. 8, 1995, vol. 332, No. 23, pp. 1560–1565.

XP–000989792, Gadi Fishman et al., "Improving Tympanic Thermometer based on a Fiberoptic Infrared Radiometer and an Otoscope and its use as a New Diagnostic Tool for Acute Otitis Media", Part of the SPIE Conf. on Lasers and Optical Technology in Otolaryngology, Jan. 1999, SPIE vol. 3590, pp. 278–286.

* cited by examiner

Primary Examiner—Max Hindenburg
(74) Attorney, Agent, or Firm—Fitch, Even, Tabin & Flannery (57) ABSTRACT

A diagnostic device and method for diagnosing an inflammatory process at an individual's middle ear. The device comprises a thermally isolated ear piece having a rear end and a front end, an energy receiving element fitted at the front end for heat pickup at a portion of the auditory canal in close proximity with the tympanic membrane. The energy receiving element is inserted into the individual's ear at a reference temperature which is lower than the individual's core temperature and an indicator is associated with the energy receiving element for indicating change in temperature with respect to time.

35 Claims, 8 Drawing Sheets

METHOD AND DEVICE FOR DIAGNOSING AN INFLAMMATORY PROCESS

FIELD OF THE INVENTION

This present invention is generally in the field of medical diagnosis, and more particularly it is concerned with a device and method for diagnosing otitis media.

BACKGROUND OF THE INVENTION

Otitis media (inflammation of the middle ear) is amongst the most frequent primary diagnosis at visits to physicians by children younger than 15 years, in the US, as reported by the American Academy of Pediatrics in the Pediatric Guidelines, Volume 94, Number 5, November 1994. In a paper entitled "Otitis Media in Children", S. Berman M. D., New England Journal of Medicine, Jun. 8, 1995, Vol. 332, No. 23, pp. 1560–1565, it is stated that approximately 17% of children under the age of three will have had three episodes of Otitis media within he past six months.

Otitis media is caused by bacteria or viruses (at times both) that enter the nose or throat and ascend the eustachian tube to reach the middle ear. This occurs when the Eustachian tube does not function properly, often because it is inflamed from a cold, sinus or throat infection, an allergy attack or owing to some other physiological disorder. Otitis media causes earache, a red inflamed eardrum (referred to interchangeably also as *tympanic membrane*), a build up of pus and mucus behind the eardrum, resulting at times in temporary hearing loss. These symptoms may all be present, or only some of which, and at different extent of appearance.

These clinical symptoms and physical signs may partially or all be present and with varying degrees of severity.

The disease is responsible for considerable morbidity, apprehension and suffering and results in extensive periods of absenteeism from work by the family.

Otitis media is the most common reason for the administration of antibiotics in childhood. It is the standard practice to prescribe antibiotics when a medical practitioner suspects otitis media.

Research on the etiology of the infection has shown that bacteria may be isolated following paracentesis of the tympanic membrane (penetration of the eardrum) in 50% of the patients. This is the basis for the widespread use of antibiotics. In a considerable number of instances, recovery is incomplete and the fluid remains within the middle ear cavity and is an ideal reservoir for re-infection (this is known as otitis media with effusion-OME). Inrecent years, the more extensive use of antibiotics has resulted in resistance of the organisms to the usual first line of therapy; as a result more extensive use of expensive broad-spectrum antibiotics has become common practice. This not only adds to the financial burden of treatment of the disease, but is also a crucial factor in promoting the further emergence of resistant bacterial strains.

The medical practitioner primarily makes the diagnosis after obtaining an appropriate history and direct examination with an otoscope, of the tympanic membrane. The membrane is translucent and normally it reflects the light'source so that a light reflex is seen. At the time of infection, there are varying degrees of redness, lack of luster and varying degrees of yellow discoloration with bulging of the tympanic membrane. All these findings indirectly reflect on the extent of the inflammation behind the tympanic membrane, that is inflammation within the middle ear.

However, the visual examination by an otoscope is often difficult to perform because of a restless patient (in particular toddlers and young children) and blocking of the external auditory canal by varying degrees of wax, resulting in poor visibility of the tympanic membrane. Furthermore, interpretation of the visual findings is dependent on the subjective assessment of the examining physician. There is therefore a distinct need for a non-invasive method to reliably diagnose the disease and quantify the extent of the inflammation.

Other examinations which are at times performed, mainly in reoccurring events, for providing the physician with information that is not learned through visual observation alone, are audiograms (hearing tests), tympanometry (measuring compliance of the tympanic membrane), pneumatic otoscopy (to assess the mobility of the tympanic membrane), blood tests to determine whether the inflammation is bacterial or viral, etc. however, these examinations are time consuming, require special facilities, expertise and laboratory equipment, all of which are expensive and unpleasant for the patient.

It is most likely that a viral disease will have lesser inflammation as opposed to a bacterial disease. Follow-up examinations which allow a quantitative assessment to be performed at each examination would be of great value in obtaining objective information as to the response to treatment and recovery of the inflammation. Therefore it would be desirable to provide a device and a method which would reliably result in a more accurate diagnosis, thus allowing the prescription of appropriate therapy and allow the correct follow up in the instance of bacterial inflation. This approach would provide the means for deciding on appropriate treatment and not the inappropriate use of antibiotic therapy. In addition to facilitating more correct clinical practice there is no question tat such a device would be more cost effective.

It will be noted that it is not an object of the present invention to measure or monitor the core temperature or the ear temperature of the patient, as known per se. Such devices are broadly disclosed, for example in U.S. Pat. No. 5,653,239.

It is thus one aspect of the present invention to provide a novel approach for diagnosis of otitis media with a method that is rapid, non-invasive and essentially pain-free. Another aspect of the invention is concerned with a diagnostic device for diagnosis of otitis media.

The device and method according to the present invention will not only detect the ailment, but will also assist in determining the extent of its severity and will enable simple and relative accurate follow-up.

SUMMARY OF THE INVENTION

According to a fist of its aspects the present invention is concerned with a diagnostic device for diagnosing an inflammatory process at an individual's middle ear, the device comprising a thermally isolated ear piece having a rear end and a front end; an energy receiving element fitted at the front end for heat pickup at a portion of the auditory canal in close proximity with the tympanic membrane; wherein the energy receiving element is inserted into the individual's ear at a reference temperature which is lower than the individual's core temperature; an indicator associated with the energy receiving element for indicating change in temperature with respect to time.

As it will become apparent hereinafter, the device may be carried out in many different embodiments and may have many forms. Setting as an example, the device may be disposable, portable-hand held or stationary.

According to a particular, preferred embodiment the energy receiving element is heat conductively connected to a sensor element extending in a direction towards said rear end. The sensor element according to this embodiment has to be at a known temperature bellow the core temperature. Typically the energy receiving element is integrally fitted at a front end of a thermally conductive sensor element extending through the ear piece towards the rear end; and where said indicator is associated with the energy receiving element.

According to one embodiment of the invention, a predetermined period of time is measured by a chemical reaction wherein upon initializing a reaction, a distinct indication appears after said predetermined period of time. One particular example is a chemical reaction involving mixing two chemical compounds with one another, whereby the indication appears after said predetermined period of time. Another example is a chemical reaction involving exposing a light sensitive agent to light or a gas sensitive agent to gas (such as oxygen contained in the air), whereby the indication appears after said predetermined period of time.

According to one embodiment the predetermined time measuring arrangement is integral with a rear portion of the device.

The indicator is adapted for generating distinctive visible or audible diagnostic signals indicating at least an inflamed condition and a non-inflamed condition. According to one example, the indicator is a substance changing its color in reaction to temperature change. This application is suitable in particular for use with disposable devices, although not limited thereto. The indicator may also be an LCD display, one or more LEDs, etc.

The indication may indicate a particular state e.g., non-inflamed, viral or bacterial inflammation. Alternatively, the indicator may provide a continuous indication by means of a scale, gradual change of color, etc. An audible signal may be generated, in addition to a visible signal, or alone. Even more so, the device and method of the invention provide a reliable aid for establishing whether a prescribed antibiotic course has succeeded.

According to one embodiment the energy receiving element and the indicator are in the form of a thermometer. By a different embodiment the energy receiving element is in the form of a thermometer and the indicator may be an LCD display.

According to a preferred design of the device the energy receiving element is of known conductive geometry where only a front portion thereof is engageable with the auditory canal. Typically the energy receiving element has a tip with a shape selected out of one of a flat, concave, convex and a spheric section.

According to still another embodiment of the invention, the ear piece is formed with a bore for visualizing the auditory canal and the tympanic membrane (as an otoscope). For that purpose it is advantageous that a light source be provided at or adjacent the rear end, for illumination of the tympanic membrane. Such a device may also be fitted with optic fibers, transferring light from a light source to the front end or an image from the front end to a visualizing element.

According to another preferred embodiment of the invention, the energy receiving element is integrally formed at an end of thermally conductive sensor element extending through the ear piece; said sensor element comprising at least one temperature transducer for measuring temperature and emitting a temperature responsive signal; the device further comprising a microcontroller for recording said signal at pre determined intervals of time and for calculating the rate of heat transfer in a direction from the energy receiving element towards the at least one temperature transducer.

Typically there are three or more temperature transducers spaced along the sensor element; each of which being connected to the micro-controller. The one or more sensor element preferably coaxially extends through the ear piece. In case the sensor element is made tubular (for visualization therethrough), the at least one temperature transducer may be annular.

Still preferably, the ear piece is fitted with a replaceable sheath conforming with the shape and size of the individual's auditory canal.

The reference temperature may be set by a peltier element associated with the device or with a heat exchanger formed with a receptacle for receiving at least a portion of the device. Such arrangements may be integral with the device or detachably connectable.

By a second of its aspects, the present invention is directed to a diagnostic method for diagnosing an inflammatory process at an individual's middle ear by determining the quantity of heat energy extracted over a predetermined period of time from the auditory canal, at a vicinity in close proximity with the tympanic membrane.

The method comprises the following steps:

(a) Cooling a heat sensing device to a reference temperature bellow the individual's core temperature;

(b) Inserting the heat sensing device into the auditory canal in close proximity with the tympanic membrane;

(c) Measuring the temperature sensed by the heat sensing device at predetermined intervals of time and coordinates;

(d) Calculating the rate of temperature change over a given period of time and generating a diagnostic signal indicative of the inflammatory state of the ear.

The reference temperature is typically in the range of between about 10 to 36° C.

For easing the insertion of the device into the individual's ear and to improve thermal conductivity, prior to step (b) a heat conductive liquid or gel-like material is applied on the temperature sensing device. The liquid material is preferably an oily substance and may comprise some therapeutic agent.

Preferably, the quantity of heat energy is measured by a device comprising a thermally isolated ear piece having a rear end and a front end; an energy receiving element fitted at the front end for heat pickup at a portion of the auditory canal in close proximity with the tympanic membrane; wherein the energy receiving element is inserted into the individual's ear at a reference temperature which is lower than the individual's core temperature; an indicator associated with the energy receiving element for indicating change in temperature with respect to time.

Although it is not an object of the invention to measure or monitor the core temperature or the ear temperature of the patient, it will be appreciated t these parameters may be measured by the device of the invention or may be incorporated therewith, for practical reasons.

BRIEF DESCRIPTION OF THE DRAWINGS

In order to understand the invention and to see how it may be carried out in practice, some preferred embodiments will now be described, by way of some non-limiting examples only, with reference to the accompanying drawings, in which:

FIGS. 1A and 1B general isometric views of a device according to one embodiment; wherein FIG. 1A is a view of the device with a replaceable sheath removed; and FIG. 1B illustrates the device in use;

DETAILED DESCRIPTION OF A PREFERRED EMBODIMENT

Figure 1A:
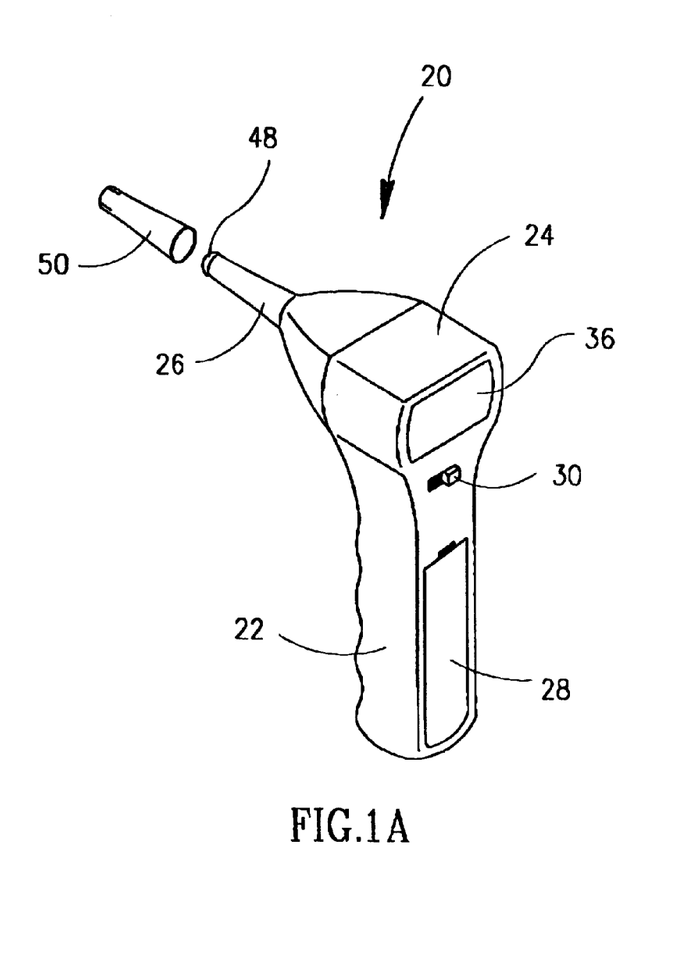
Figure 1B:
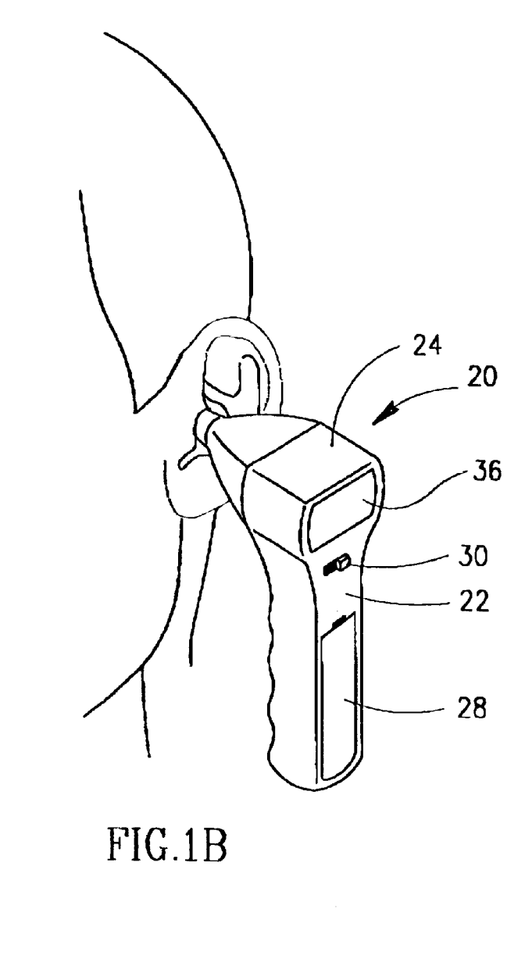

Attention is first directed to FIGS. 1A and 1B in which a diagnostic device according to the invention is generally designated 20 and comprises a body/handle portion 22 a head portion 24 and an ear piece portion 26.

Body portion 22 comprises a battery compartment formed with a removable cover 28 and an operating switch 30, serving also as a reset switch. Head portion 24 comprises an LCD 36 and a CPU (see FIG. 2). The ear piece 26 has a conical shape conforming with the shape of the auditory canal 40 of an individual's ear 44 (FIG. 2), and an energy receiving element 48. A removable sheath 50 is provided (FIG. 1A) for hygienic care and for adapting the size and shape of the ear piece to the individual's ear. It is appreciated that sheath 50 may be omitted. As will become apparent hereinafter, ear piece 26 (apart from its tip) and shaft 50 are made of a thermally isolated material.

Figure 2:
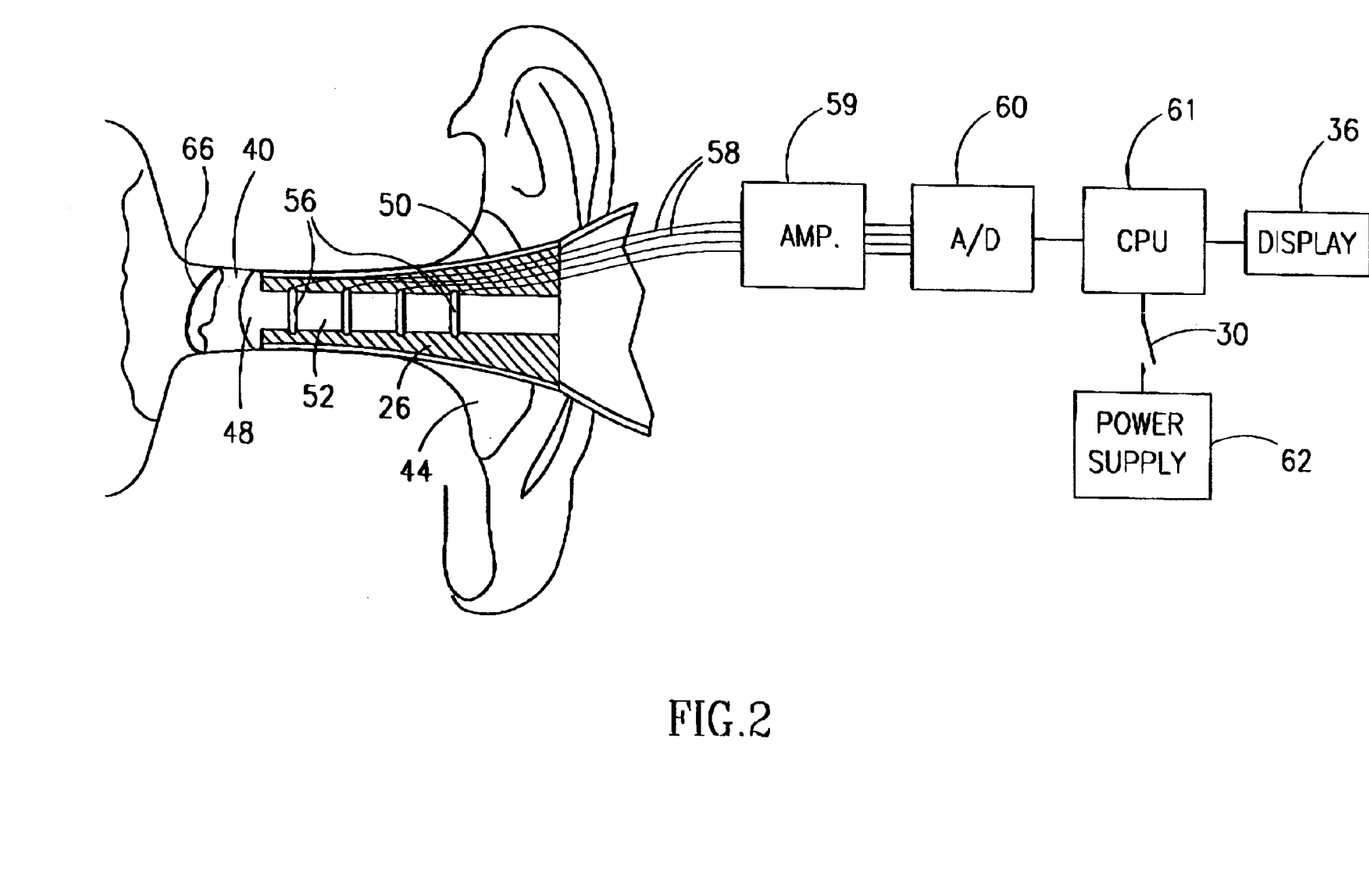
FIG. 2 is a schematic illustration of the principal components of the device according the present invention, illustrating how it is used with respect to a patient's ear.

Further attention is made to FIG. 2 which is partially schematic and illustrates some of the principal components which include a sensor element 52 integrally extending backwards from the energy receiving element 48 and has a cylindrical shape, being tightly enveloped by ear piece 26. The energy receiving element 48 with its associated sensor element 52 are made of a martial having low thermal resistance (high thermal coefficient of conductivity). A plurality of temperature transducers (thermocouples, resistive temperature devices-RTD, thermisters, thin film resistive transducers, etc.) 56 (four in the present example) are fixed along the sensor element 52, each being electrically connected by wires 58 to an amplifier 59, connected in series to an A/D converter 60, and to a CPU 61. The CPU is electrically connected with the power supply 62 (batteries received within handle 22) via switch 30 and to the LCD display 36. Possibly there is also provided screen (LCD) illumination. However, the artisan will appreciate that this is merely one schematic representation and that other arrangements are suitable too.

The method of the invention is such that prior to using the device, the energy receiving element 48 together with the sensor element 52 are brought to a known reference temperature of distribution which is either constant or varying along the sensor element and which below the individual's core temperature, i.e. in the range of between about 20–36° C., preferably about 20° C. although lower temperatures are possible too. Such cooling is carried out in different ways as will be explained later below. Then, the device is inserted into the auditory canal 40 such that the energy receiving element 48 is at a distance not closer than about 1 mm. from the tympanic membrane 66 (FIG. 2) so as to avoid unpleasant feeling if accidentally encountered by the fore end of the energy receiving element 48. At times a lubricating substance may be applied on to the energy receiving element 48, which substance may also comprise anaesthetic and disinfectant agents.

Upon activating the device by switch 30, a series of rapid recordings (governed by the A/D converter 60) are picked up by the transducers 56 at predetermined intervals of time (typically measured in milliseconds) which are then fed through the amplifier 59 and the A/D converter 60 into the CPU 61 for calculating the heat flow, namely, the change of temperature versus time. This is calculated by using the differential equation shown in Equation (1) governing heat flow in a two dimensional body, and solving it using a lumped capacity backward difference numerical technique, as shown in Equation (2). The heat energy $q_1$ in Equation (2) transferred into the sensor element 52 can then be calculated. The time dependent boundary conditions from data obtained in the sensor element 52 are used to adjust the calculations together with the conductive and convective boundary conditions of the energy receiving element 48 which is in contact with the auditory canal 40. This adjustment provides correlation to the actual conditions of the sensor element 52 so that the energy transferred per unit time (Equation 2, quantity $q_i$) can be obtained.

$$k\left(\frac{\partial^2 T}{\partial x^2} + \frac{\partial^2 T}{\partial y^2}\right) = pc\frac{\partial T}{\partial \tau} \qquad (1)$$

Where: k=coefficient of conduction (W/m° C.)
P=density kg/m³)
c=specific heat (J/Kg° C.)
τ=time (s)

$$T_i^{p+1} = \frac{q_i + \sum_i (T_j^{p+1}/R_{ij}) + (C_i/\Delta\tau)T_i^p}{\sum_j (1/R_{ij}) + C_i/\Delta\tau} \qquad (2)$$

Where: i=node at which temperature T is calculated
j=the nodes adjoining i
$q_i$=heat delivered to node i by heat generation
$\Delta_\tau$=time increment (s)
$R_{ij}$ lumped resistance between the ith and jth node (determined by geometry and material coefficient of conduction of the energy receiving element and the sensor element)
$C_i$=lumped capacity of the ith node (determined by the specific heat capacity of the energy receiving element and the sensor element and their geomety)

Test results were made and were then processed so as to determine the conditions defining different stages of inflammatory processes. The data derived from these tests was processed according to the follow chart shown in FIG. 3 in which the diagnostic procedure begins at block 80 with the insertion of the ear piece 26 into the patient's ear 44. In order to capture the heat from a position proximate the tympanic membrane, as a function of time, the sensor element 52 transducers' 56 readings are stored in a memory site associate with the CPU 60.

Figure 3:
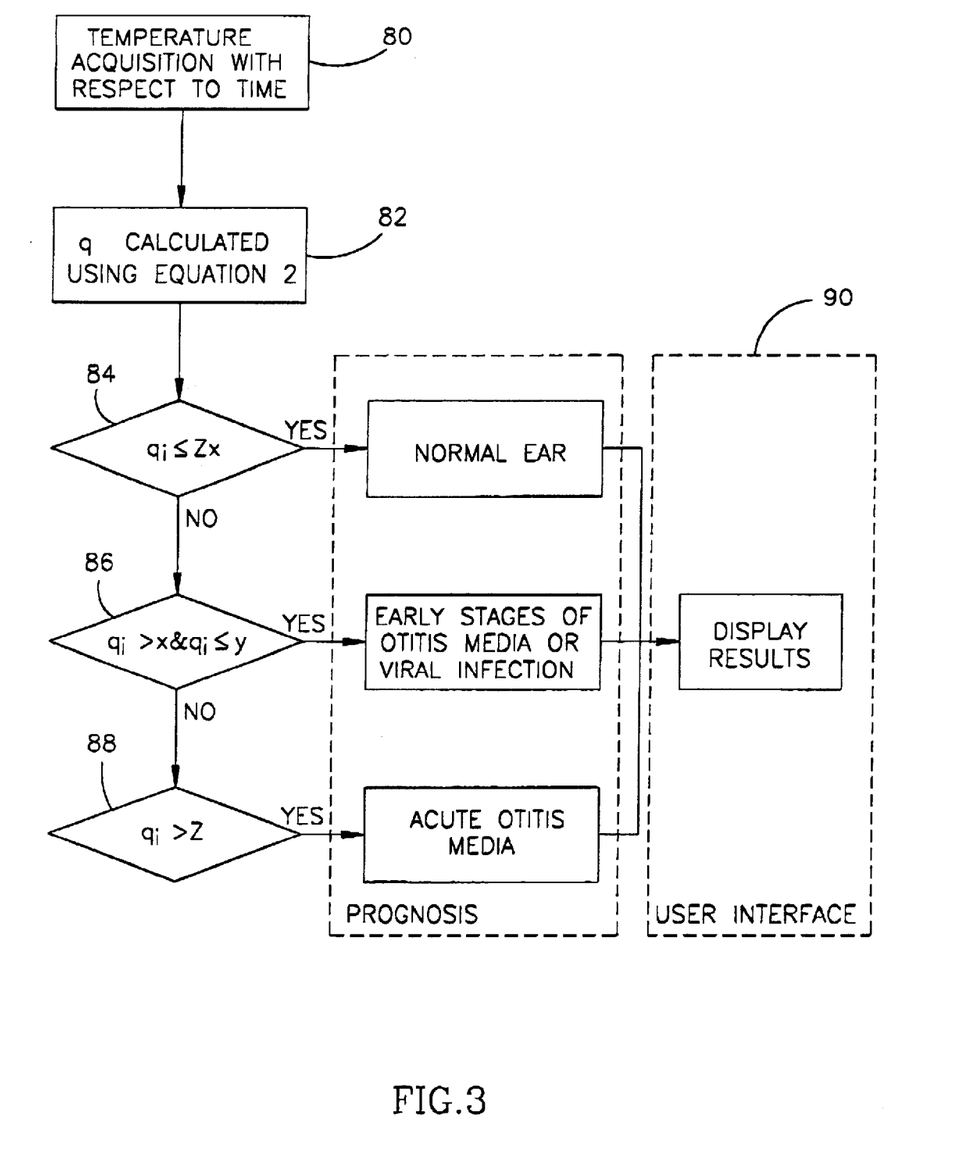
FIG. 3 is a flow chart illustrating the processing steps of the test results.

In block 82, the numerical method of the above equations is applied using the single or multiple point temperatures captured and stored in the memory at a point in time, together with the particular geometry of sensor element 52, the thermal properties and particular geometry of energy receiving element 48, and the ear canal boundary conditions. The numerical method as described in Equation (2) above provides the quantity $q_i$, which is the amount of heat delivered to a node i by heat transfer. Once the value of $q_i$ is established, decision blocks 84, 86 and 88 is processed to determine which of them is true by comparison if the value of $q_i$ is with the limits prescribed.

If the comparison is true in block 84, a normal ear heat transfer rate is determined. If the comparison is true in block 86, the rate of heat transfer is determined to be that which represents inflammation equivalent to a middle ear exhibiting early stages of otitis media. If the comparison is true in block 88, the rate of heat transfer is detained to be that repress inflammation indicating acute otitis media. However, additional intermediate ranges hay be calculated and indicated as well.

Figure 4:
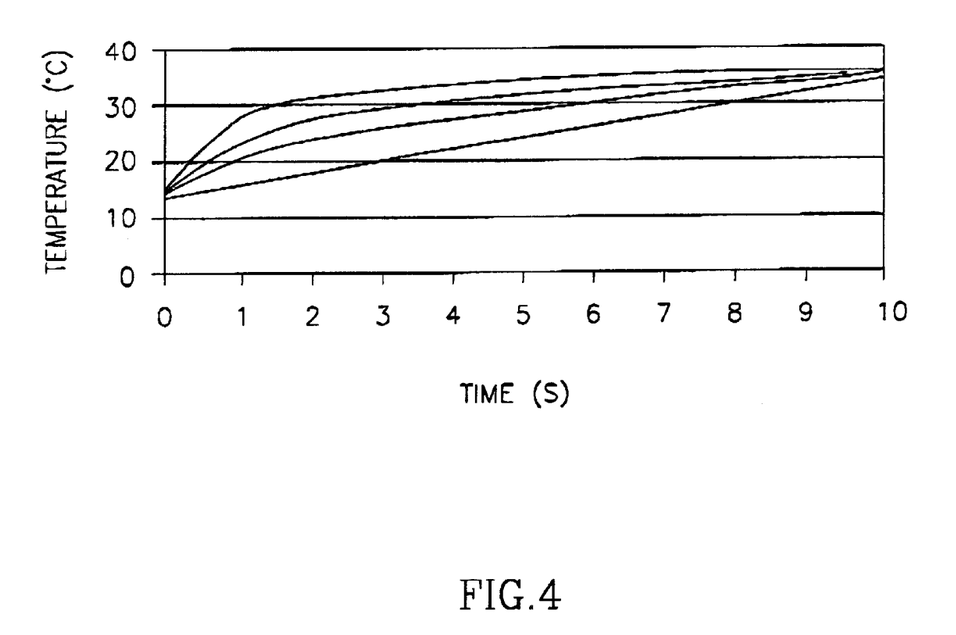
FIG. 4 is a graph representing axial temperature distribution along a sensor element.

The graph of FIG. 4 is constructed by capturing the temperature distribution along the sensor element 52, with respect to time and it represents raw data collected simultaneously from two or more independent temperature transducers 56. Any parameter on the time dependent temperature curve of FIG. 4 can be used as a basis for extracting x, y and z in the flow chart of FIG. 3 (for. example a value of temperature at an instance in time, the shape of the temperature time curve or the temperature/ probe position curve, or the area under the said curves etc).

The values of x, y and z can also be established after clinically testing the specific probe design and assigning the values of x, y and z from the tests from a statistically significant sample of test patients.

In block 90 of FIG. 3, the results of the processing of blocks 84, 86 and 88 are displayed on a user interface, e.g. display 36 in FIGS. 1 and 2. This interface can be a variety of other arrangements, e.g. a LED light indication, a color chart representing colors equivalent to chemical color changes when exposed to temperature, a scaled meter, etc.

Figure 5A:
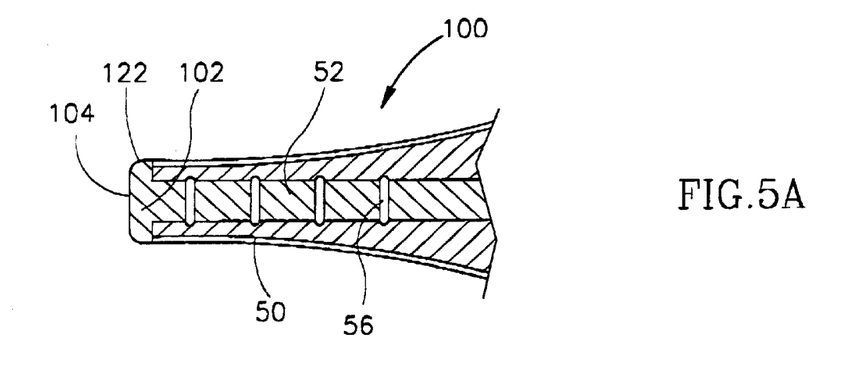
FIGS. 5A–5C illustrate ear tips with different designs of energy receiving elements.
Figure 5B:
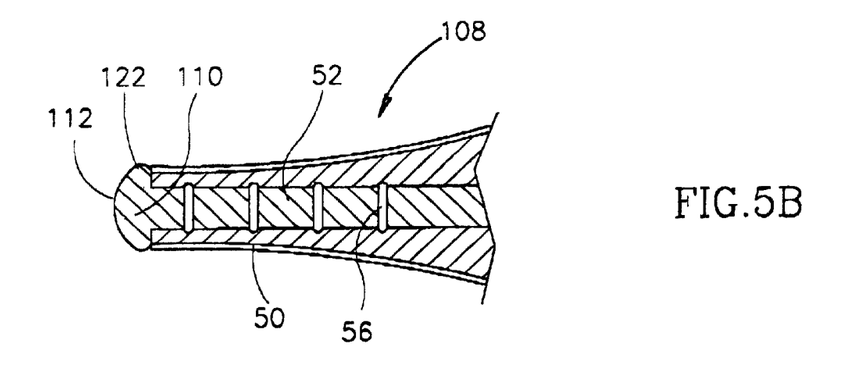
Figure 5C:
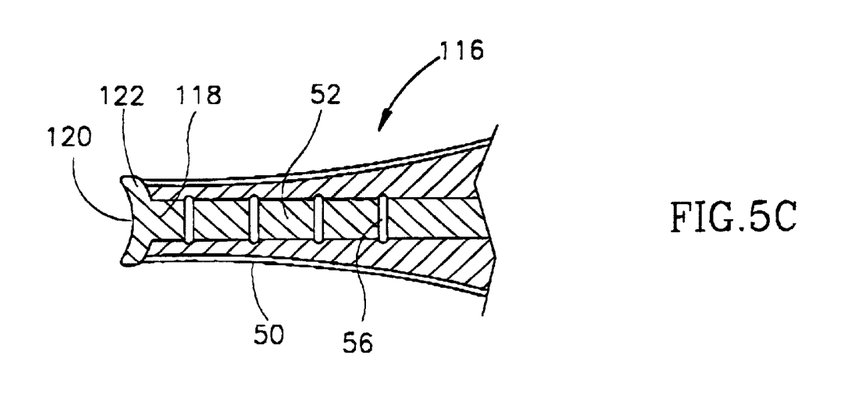

Further attention is now directed to FIG. 5 of the drawings showing different forms of ear pieces. In FIG. 5A the ear piece generally designated 100 has an energy receiving element 102 integral with the sensor element 52 where the energy receiving element has an essentially fore-end 104 with rounded edges to prevent injury of the auditory canal. A similar ear piece 108 is seen in FIG. 5B wherein the energy receiving element 110 has a convex front end 112 which in fact is a portion of a sphere. In FIG. 5C the ear tip 116 has a energy receiving element 118 with a concave front end 120. It is noted that in all of the embodiments of FIG. 5, a rim 122 of the respective-energy receiving element 102, 110 and 118 is flush or slightly larger than the edge of the sheath 50, so as to ensure adequate heat conductivity between the auditory canal 40 (FIG. 2) and the energy receiving element.

It is also noted that each of the sensor elements 52 in the embodiments of FIG. 5 are similar and are each provided with a plurality of temperature transducers 56 as explained hereinbefore with reference to FIG. 2.

Figure 6:
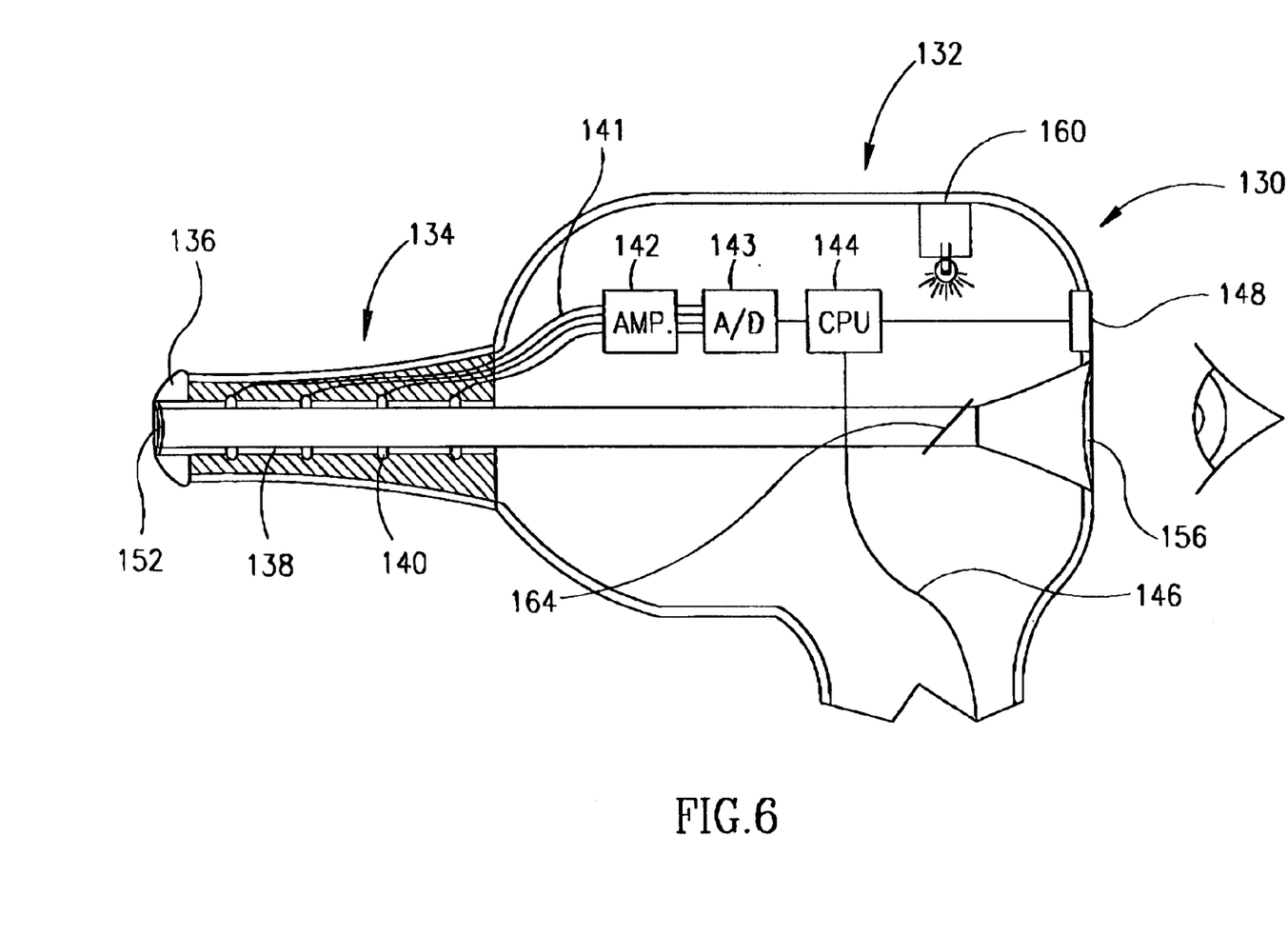
FIG. 6 is a perspective view of a disposal device according to an embodiment of the invention.

The device 130 seen in FIG. 6 is an improved version of the embodiment of FIGS. 1 and 2 showing only a head portion 132 and ear piece 134 of the device. Ear piece 134 has an energy receiving element 136 from which extends backwards a sensor element 138 fitted with four temperature transducers 140 electrically connected by electric wires 141 to CPU 144 via an amplifier 142 and an A/D converter 143, the CPU 144 being connected also to a power supply (not shown) by wiring 146 and an operating switch 148, as explained hereinabove with reference to FIG. 2.

However, energy receiving element 136 and sensor element 138 are formed with a through going bore 152 extending towards a rear end of the device and fitted with a eye piece 156. An illuminating bulb 160 is formed within the head portion 132 and a suitable reflecting mirror 164 directs the light through the bore 152. This arrangement allows simultaneous visual inspection of the auditory canal and the tynpanic membrane.

Although not shown, the illuminating device 160 is typically connected to the power supply and is activated by a suitable switch. Furthermore, rather than a visualizing bore 152, there may be provided a fiber optic transferring light towards the front end of the device and transferring an image to the eye piece 156.

Figure 7:
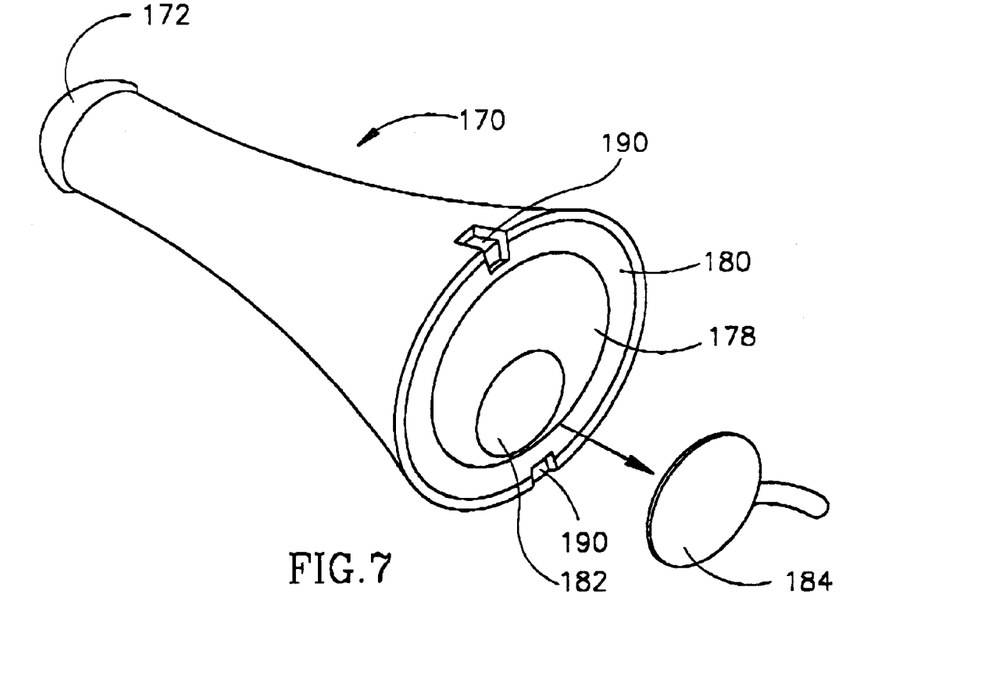
FIG. 7 is sectional view of the device seen in FIG. 4.
Figure 8:
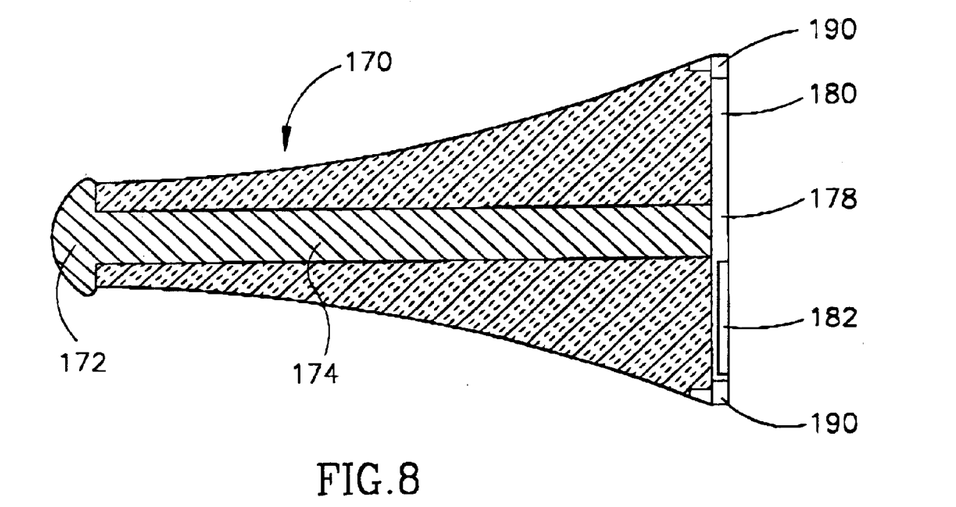
FIG. 8 is a sectional view of a portion of a hand-held device according to the invention, serving also as an otoscope.

FIGS. 7 and 8 illustrate a different application of a device in accordance with the present invention generally designated 170. The device is disposable and does not comprise any electric components. It has the general shape of an ear piece with an energy receiving element 172 integrally formed with a sensor element 174 rearwardly extending through the themally isolated ear piece and terminating at a chemical indicator 178 formed at a rear face 180 of the device. Chemical indicator 178 is a thermochromic liquid crystal (TLC) which is a chemical substance changing its color responsive to temperature change.

A chemical reaction time indicator 182 is also formed at the rear end 180 and is a priori sealed by a removable foil 184.

Time indicator 182 may be of different types. One such example is a photosensitive chemical substance which upon exposure to light, after a predetermined period of time changes its color. Another example is such a device which upon exposure to air (oxygen in particular) it changes its color after a predetermined period of time. Other possible forms are for example two chemical compounds which are maintained separate from one another until activation by mixing thereof (e.g. by piercing a membrane between two containers holding such fluid substances, etc.).

The arrangement in accordance with the embodiment of FIGS. 7 and 8 is such that the device is first cooled to a temperature below the patient's core temperature. A comfortable temperature is in the range of about 10 to 30° C. Such cooling may be obtained by different means such as immersing the device within a container holding ice water, storing the device for a period of time in a refrigerator or by a Peltier-type cooling device as will be explained hereinafter. When the device in fact the energy receiving element 172 and sensor element 174 have reached the reference temperature, the foil 184 is removed and the device is inserted into the patient's ear to a distance not closer tan about 1 mm from the tympanic membrane. As the time indicator 182 changes its color, as a result of exposure to light or to oxygen, as explained hereinabove, the device is withdrawn from the patient's ear and the chemical indicator 178 is visualized to determine its indication which may have, for example, three situations, namely a first situation in which it shows a green color, indicating no inflammation of the middle ear, an orange color indicating a light inflammation of the middle ear, and a red color indicating otitis media.

It will be appreciated that the shape and size of the ear piece 170 is fitted for insertion into a patient's ear and different such devices may be provided for patients of different ages. In addition, the method of indicating the change in temperature and mu g the predetermined period of time may also vary in accordance with the different embodiments. Furthermore, the color indicator may be suitable for indicating a range of inflammatory stages, represented by different colors.

Figure 10:
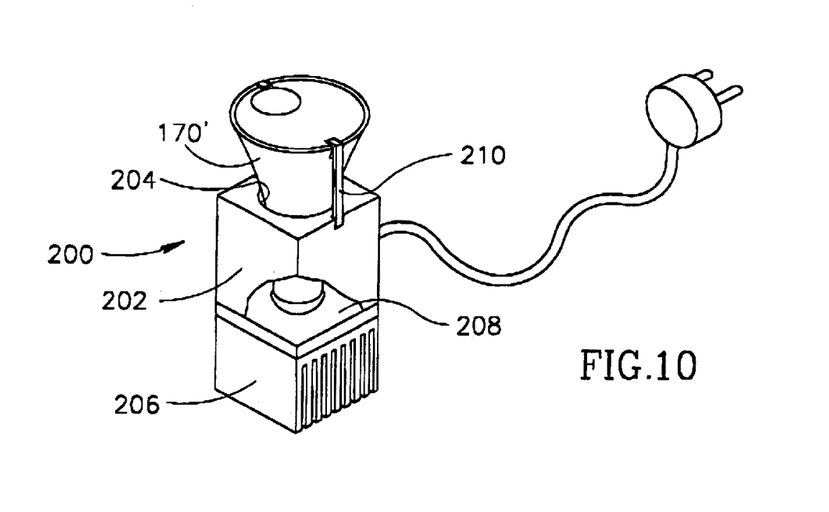
FIG. 10 is an isometric view, partially cutout, of a Peltier-type cooling device for use with several types of devices according to the invention.

As noted in FIGS. 7 and 8, device 170 is formed with two opposed recesses 190, the purpose of which will become apparent hereinafter with reference to FIG. 10.

Figure 9:
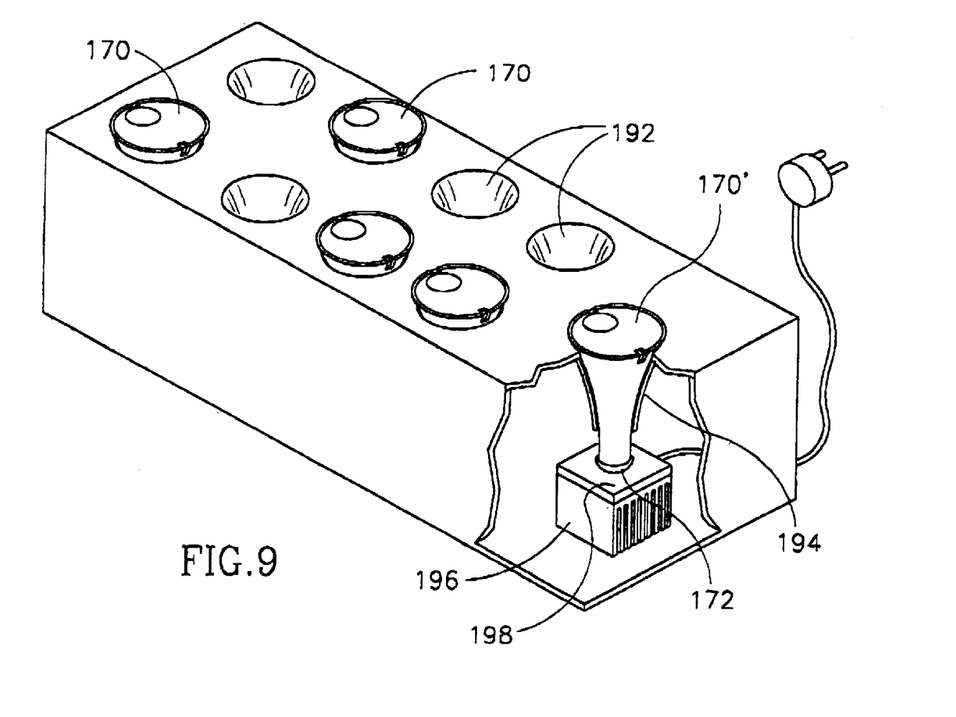
FIG. 9 is an isometric view, partially cutout, of a container holding a plurality of devices of the type seen in FIG. 4, and comprising a Peltier-type cooling arrangement.

FIG. 9 is a holding and cooling container for use in conjunction with the disposable (or not disposable) ear pieces 170 of FIGS. 7 and 8. The container comprises eight storage receptacles 192 adapted for receiving ear pieces 170 and as seen in the picture, four of these receptacles are occupied. A cooling receptacle 194 is formed above a Peltier-type cooling element 196 whereby a device 170' received within receptacle 194 comes to rest over the cooling element 196 with energy receiving element 172 engaging top surface 198 of the cooling element 196. In this way the device 170' is cooled to the reference temperature as explained hereinabove.

The cooling device 200 seen in FIG. 2 is adapted for use with either a disposable device 170' which is similar to device 170 of FIGS. 7 and 8 and is also suitable for use with a hand-held device of the kind seen in FIGS. 1 and 6. The device comprises a housing 202 formed with a receptacle 204 and a Peltier-type cooling element 206 formed with a conductive cooling plate 208. A latch member 210 is pivotally attached to the housing 202 and is adted for snap engagement with recesses 190 of the device 170 (see FIGS. 7 and 8). In a similar manner, the device may be connected also to the ear piece 134 of the device seen in FIG. 6 or to the ear piece 26 of the device seen in FIG. 1.

It will be appreciated to a person skilled in the art that many varieties of cooling arrangements are available.

Although not shown, it will also be appreciated that the device in accordance with the present invention may also serve as a thermometer for measuring the core temperature of the individual, although this is not the main aim of the device. Such temperature measurements may be performed either by thermochromic liquid crystals applied on the device (either disposable or not) or may be a dedicated thermocouple for providing such information. Alternatively, the hand-held device, such as that seen in FIGS. 1, may be provided with an IR temperature measuring device as known per se.

Furthermore, it will be appreciated that the device many be connected to a processor such as a personal computer (not shown). This might be usefull for storage of medical data of an individual, for obtaining and processing data for research, etc. Such data may also be derived by using a hand-held device. of the type seen in FIG. 1 and transferring data to a PC by a suitable communication socket, etc. Alternatively, the device is connected to a PC by suitable wiring as known per se.

Whilst preferred embodiments have been shown and described, it is to be understood that it is not intended thereby to limit the disclosure of the invention, but rather it is intended to cover all modifications and arrangements falling within the spirit and the scope of the invention, *mutatis muandis*.

What is claimed is:

1. A diagnostic device for diagnosing an inflammatory process at an individual's middle ear by determining a quantity of heat energy extracted from his auditory canal over a period of time, the device comprising a thermally isolated ear piece having a rear end and a front end; an energy receiving element fitted at the front end for receiving heat emanating from a portion of the auditory canal in close proximity to the tympanic membrane of the ear; wherein the energy receiving element is inserted into the individual's ear at a predetermined reference temperature which is lower than the individual's core temperature; and an indicator associated with the energy receiving element for indicating change in temperature with respect to time.

2. A diagnostic device according to claim 1, wherein the energy receiving element is heat conductively connected to a sensor element extending in a direction towards said rear end.

3. A diagnostic device according to claim 1, wherein the energy receiving element is integrally fitted at a front end of therally conductive sensor element extending through the car piece towards the rear end; and where said indicator is associated with the energy receiving element.

4. A diagnostic device according to claim 1, wherein a predetermined period of time is measured by a chemical reaction wherein upon initialing a reaction, a distinct indication appears after said predetermined period of time.

5. A diagnostic device according to claim 4, wherein the predetermined period of time is measured by a chemical reaction involving mixing two chemical compounds with one another, whereby the indication appears after said predetermined period of time.

6. A diagnostic device according to claim 4, wherein the predetermined period of time is measured by a chemical reaction involving exposing a light sensitive agent to light, whereby the indication appears after said predetermined period of time.

7. A diagnostic device according to claim 4, wherein the predetermined time measuring arrangement is integral with a rear portion of the device.

8. A diagnostic device according to claim 1, wherein the indicator is a substance changing its color in reaction to temperature change.

9. A diagnostic device according to claim 1, wherein at least a front portion of the energy receiving element is engageable with the auditory canal.

10. A diagnostic device according to claim 9, wherein the heat is determined by an energy receiving element and a sensor element, both of known conductive coefficients and geometry.

11. A diagnostic device according to claim 1 being a disposable device.

12. A diagnostic device according to claim 1, wherein the ear piece is formed with a bore for visualizing the auditory canal and the tympanic membrane.

13. A diagnostic device according to claim 12, comprising a light source at or adjacent the rear end.

14. A diagnostic device according to claim 1, wherein the ear piece is fitted with optic fibers, transferring light from a light source to the front end or an image from the front end to a visualizing element.

15. A diagnostic device according to claim 10, wherein the energy receiving element has a tip with a shape selected out of one of a flat concave, convex and a spheric section.

16. A diagnostic device according to claim 1, wherein the energy receiving element is integrally formed at an end of themally conductive sensor element extending through the ear piece; said sensor element comprising at least one temperature transducer for measuring temperature and emitting a temperature responsive signal; the device further comprising a micro-controller for recording said signal at pre determined intervals of time and for calculating the rate of heat transfer in a direction from the energy receiving element towards the at least one temperature transducer.

17. A diagnostic device according to claim 16, wherein three or more temperature transducers are spaced along the sensor element; each of said temperature transducers being connected to the micro-controller.

18. A diagnostic device according to claim 16, wherein the sensor element coaxially extends through the ear piece.

19. A diagnostic device according to claim 17, wherein the sensor element is tubular and the at least one temperature transducer annular.

20. A diagnostic device according to claim 1, wherein the energy receiving element is insertable to a distance not closer than about 1 mm from the tympanic membrane.

21. A diagnostic device according to claim 16, wherein the ear piece is fitted with a replaceable sheath conforming with the shape and size of the individual's auditory canal.

22. A diagnostic device according to claim 1, wherein the reference temperature is set by a peltier element associated with the device or with a heat exchanger formed with a receptacle for receiving at least a portion of the device.

23. A diagnostic device according to claim 22, wherein the reference temperature is set by at least one heat exchanger fitted within a container sized for retaining one or more such devices, with a receptacle for engaging at least the energy receiving element.

24. A diagnostic device according to claim 1, wherein the indicator is adapted for generating distinctive visible or audible diagnostic signals indicating at least an inflamed condition and a non-inflamed condition.

25. A diagnostic device according to claim 1, wherein the indicator is adapted for indicating a continuous range of inflammatory stages.

26. A diagnostic device according to claim 16, being hand held wherein the ear piece is mounted at an end of a handle member fitted with an electric source of energy.

27. A diagnostic device according to claim 1, further comprising a temperature measuring and indicating device for indicating the individual's core temperature.

28. A diagnostic device according to claim 16, connectable to a memory storage device for recordation of the individual's diagnosis.

29. A diagnostic method for diagnosing an inflammatory process at an individual's middle ear by determining the quantity of heat energy received by a heat sensing device over a predetermined period of time from the auditory canal, at a vicinity in close proximity to the tympanic membrane of the ear, the method comprising the following steps:

(a) cooling a heat sensing device to a predetermined reference temperature below an individual's core temperature;

(b) inserting the heat sensing device into the auditory canal in close proximity with a tympanic membrane;

(c) measuring a temperature sensed by the sensing device within predetermined intervals of time and coordinates; and (d) calculating a rate of temperature change over a given period of time and generating a diagnostic signal indicative of an inflammatory state of the ear.

30. A method according to claim 29, wherein prior to step (b) a heat conductive liquid or gel-like material is applied on the temperature sensing device.

31. A method according to claim 30, wherein the liquid material is an oily substance.

32. A diagnostic method according to claim 29, wherein the quantity of heat energy is measured by a device comprising a thermally isolated ear piece having a rear end and a front end; an energy receiving element fitted at the front end for receiving heat emanating from a portion of the auditory canal in close proximity to the tympanic membrane; wherein the energy receiving element is inserted into the individual's ear at a predetermined reference temperature which is lower than the individual's core temperature; and an indicator associated with the energy receiving element for indicating change in temperature with respect to time.

33. A method according to claim 29, wherein the temperature is measured by an energy receiving element of known conductive geometry.

34. A method according to claim 29, wherein the reference temperature is in the range of between 20 to 36° C.

35. A method according to claim 29, wherein the predetermined period of time is measured using a time indicating device.

* * * * *